United States Patent
Soma et al.

(10) Patent No.: US 8,536,258 B2
(45) Date of Patent: Sep. 17, 2013

(54) STABILIZER AND METHOD OF MANUFACTURING THE SAME, THERMOPLASTIC POLYMER COMPOSITION USING THE SAME, AND METHOD OF STABILIZING THERMOPLASTIC POLYMER

(75) Inventors: Ryoji Soma, Nara (JP); Kenji Kimura, Toyonaka (JP); Masatsugu Akiba, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 625 days.

(21) Appl. No.: 12/219,145

(22) Filed: Jul. 16, 2008

(65) Prior Publication Data

US 2009/0030127 A1    Jan. 29, 2009

(30) Foreign Application Priority Data

Jul. 20, 2007    (JP) ................. 2007-189738

(51) Int. Cl.
*C08K 5/00*    (2006.01)
*C08K 5/09*    (2006.01)
*C09K 15/00*    (2006.01)

(52) U.S. Cl.
USPC .......... 524/291; 524/299; 524/349; 252/404; 560/130; 560/140

(58) Field of Classification Search
USPC .............. 524/293, 291, 302, 289, 294, 299, 524/349; 528/193, 206; 436/161; 210/656, 210/198.2; 560/130, 140, 183, 225; 252/404
See application file for complete search history.

(56) References Cited

U.S. PATENT DOCUMENTS

| | | | |
|---|---|---|---|
| 3,984,372 A | | 10/1976 | Cottman |
| 4,365,032 A | * | 12/1982 | Yosizato et al. ............... 524/99 |
| 4,774,274 A | | 9/1988 | Takata et al. |
| 5,128,398 A | | 7/1992 | Sasaki et al. |
| 5,214,193 A | * | 5/1993 | Inoue et al. .................. 560/140 |
| 6,861,552 B2 | | 3/2005 | Yamamoto et al. |
| 2004/0015008 A1 | | 1/2004 | Yamamoto et al. |

FOREIGN PATENT DOCUMENTS

| | | |
|---|---|---|
| CA | 2026900 | 4/1991 |
| CN | 1446190 A | 10/2003 |
| EP | 0144 477 A1 | 6/1985 |
| EP | 0 322 166 A1 | 6/1989 |
| EP | 1 306 363 A1 * | 5/2003 |
| EP | 1 306 636 A1 | 5/2003 |
| GB | 2042 512 A | 9/1980 |
| JP | 1-168643 | 7/1989 |
| JP | 3-88841 | 4/1991 |
| JP | 03-207788 | 9/1991 |
| JP | 04-264051 | 9/1992 |
| JP | 4-327558 | 11/1992 |
| JP | 2000-143873 | 5/2000 |
| JP | 2006-176419 | 7/2006 |

OTHER PUBLICATIONS

Notice of Allowance in U.S. Appl. No. 12/219,384 dated Mar. 18, 2011.
Office Action in CN Appln No. 200810137786.6 dated Jul. 14, 2011.
Notice of Grounds of Rejection in JP Appln No. 2008-186221 dated Jan. 31, 2012.
Summons to Attend Oral Proceedings Pursuant to Rule 115(1) EPC—European Application No. 08160516.4 dated Jul. 2, 2010.
European Search Report EP 08 16 0882 dated Oct. 21, 2008.
Third Office Action Chinese Patent Application No. 200810137786.6 dated Mar. 12, 2012.
Third Office Action Chinese Patent Application No. 200810137786.6 dated Jan. 14, 2013.

* cited by examiner

*Primary Examiner* — Hannah Pak
(74) *Attorney, Agent, or Firm* — Foley & Lardner LLP

(57) ABSTRACT

The present invention provides a stabilizer containing, as a main component, a bisphenol monoester and a bisphenol-based compound, wherein the area of the bisphenol-based compound is 0.15 to 70 when the area of the bisphenol monoester is set to be 100 in a chromatograph obtained by liquid chromatography analysis of the stabilizer, a method of manufacturing the same, a thermoplastic polymer composition containing the stabilizer, as well as a stabilizer that can further improve the process stability of the thermoplastic polymer, as compared with the conventional one, by compounding the stabilizer into the thermoplastic polymer through a method of stabilizing the thermoplastic polymer using the stabilizer and a method of manufacturing the stabilizer.

6 Claims, 3 Drawing Sheets

STABILIZER AND METHOD OF MANUFACTURING THE SAME, THERMOPLASTIC POLYMER COMPOSITION USING THE SAME, AND METHOD OF STABILIZING THERMOPLASTIC POLYMER

BACKGROUND OF THE INVENTION

1. Field of the Invention

The present invention relates to a stabilizer, a method of manufacturing the same, a thermoplastic polymer composition using the stabilizer, and a method of stabilizing a thermoplastic polymer.

2. Description of the Background Art

In order to improve physical properties such as process stability, elasticity, adhesiveness, impact resistance, coloring resistance, and heat resistance of a thermoplastic polymer such as polypropylene and polystyrene, a bisphenol monoester represented by the following Formula (1):

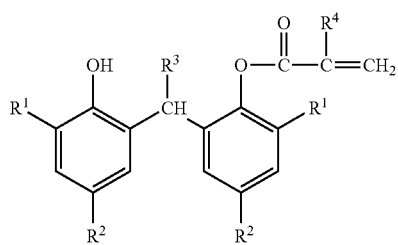

(1)

wherein each $R^1$ and $R^2$ independently represents an alkyl group having 1 to 5 carbon atoms, $R^3$ represents a hydrogen atom or an alkyl group having 1 to 3 carbon atoms, and $R^4$ represents a hydrogen atom or a methyl group, has been compounded as a stabilizer (for example, refer to Japanese Patent Laying-Open No. 01-168643 (Patent Document 1) and Japanese Patent Laying-Open No. 03-88841 (Patent Document 2)).

In general, since there is a possibility that existence of a small amount of impurities in a stabilizer adversely affects stabilization performance including process stability, a stabilizer that is purified at a high purity so that impurities are not contained is available commercially and used. For example, a bisphenol monoester that is purified so as to be almost completely pure using a purification method disclosed in Japanese Patent Laying-Open No. 04-327558 (Patent Document 3) is available commercially and used as a stabilizer.

SUMMARY OF THE INVENTION

An object of the present invention is to provide a stabilizer capable of further improving process stability of a thermoplastic polymer compared with the conventional one by compounding the stabilizer into the thermoplastic polymer, and a method of manufacturing the same.

The stabilizer of the present invention contains, as a main component, a bisphenol monoester represented by the following Formula (1):

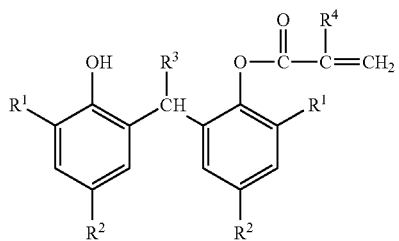

(1)

wherein each $R^1$ and $R^2$ independently represents an alkyl group having 1 to 5 carbon atoms, $R^3$ represents a hydrogen atom or an alkyl group having 1 to 3 carbon atoms, and $R^4$ represents a hydrogen atom or a methyl group, and a bisphenol-based compound represented by the following Formula (2):

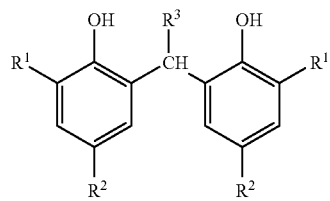

(2)

wherein $R^1$ to $R^3$ are the same as described above, and is characterized in that the area of the bisphenol-based compound represented by the Formula (2) is 0.15 to 70 when the area of the bisphenol monoester represented by the Formula (1) is set to be 100 in a chromatograph obtained by liquid chromatography analysis of the stabilizer.

In the stabilizer of the present invention, the total amount of the bisphenol monoester represented by the Formula (1) and the bisphenol-based compound represented by the Formula (2) per 100 parts by weight of the stabilizer is preferably 95 parts by weight or more.

The present invention is a method of manufacturing the above-described stabilizer of the present invention including the steps of mixing the bisphenol monoester represented by the Formula (1) and the bisphenol-based compound represented by the Formula (2), and adjusting the amounts of the bisphenol monoester represented by the Formula (1) and the bisphenol-based compound represented by the Formula (2) so that the area of the bisphenol-based compound represented by the Formula (2), to be mixed, is 0.15 to 70 when the area of the bisphenol monoester represented by the Formula (1) is set to be 100 in a chromatograph obtained by liquid chromatography analysis of the obtained mixture.

In the method of manufacturing a stabilizer according to the present invention, 0.1 to 45 parts by weight of the bisphenol-based compound represented by the Formula (2) is preferably mixed into 100 parts by weight of the bisphenol monoester represented by the Formula (1).

The present invention is also a method of manufacturing the above-described stabilizer of the present invention including the step of carrying out esterification reaction of the bisphenol-based compound represented by the following Formula (2):

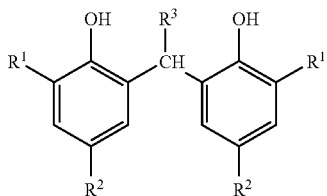

(2)

and a carboxylic acid-based compound represented by the following Formula (3):

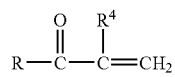

(3)

wherein $R^4$ is the same as described above, R represents a hydroxy group, a halogen atom, an alkoxy group having 1 to 4 carbon atoms, or a group represented by the following Formula (4):

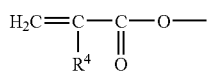

(4)

wherein $R^4$ is the same as described above, wherein 0.3 to 0.6 mol of the carboxylic acid-based compound represented by the Formula (3) is used with respect to 1 mol of the bisphenol-based compound represented by the Formula (2).

The present invention also provides a thermoplastic polymer composition containing 0.01 to 5 parts by weight of the stabilizer with respect to 100 parts by weight of the thermoplastic polymer.

The present invention further provides a method of stabilizing a thermoplastic polymer containing 0.01 to 5 parts by weight of the stabilizer according to the present invention with respect to 100 parts by weight of the thermoplastic polymer.

According to the present invention, a stabilizer can be provided that can improve the process stability of a thermoplastic polymer synergistically by compounding the stabilizer into the thermoplastic polymer compared with the case of using the bisphenol monoester represented by the Formula (1) and the bisphenol-based compound represented by the Formula (2) separately. Further, by using such a stabilizer of the present invention, a thermoplastic polymer composition in which the process stability is improved compared with the conventional one, and also a method of stabilizing the thermoplastic polymer that can improve the process stability compared with the conventional one, can be provided.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
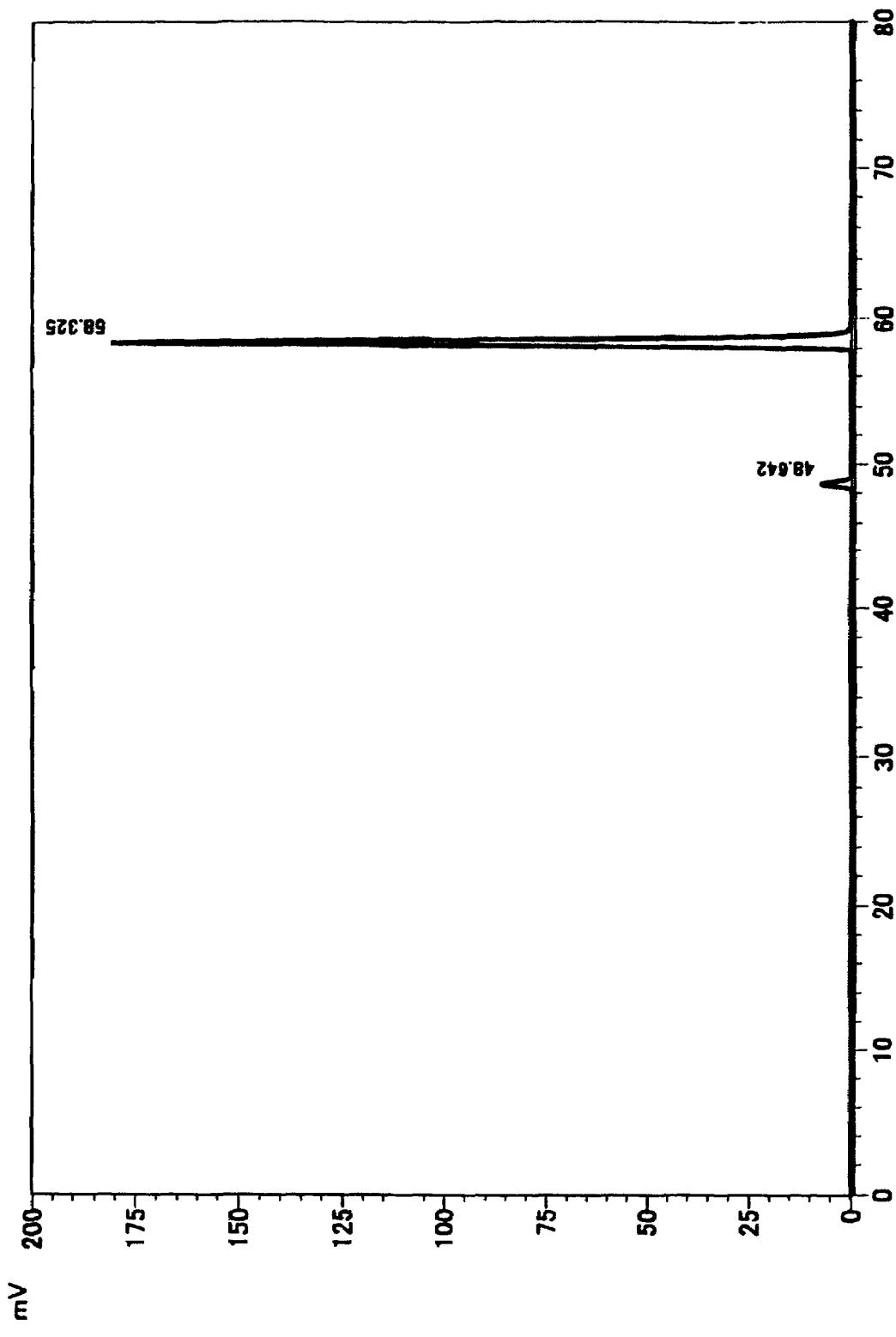
FIG. 1 is a liquid chromatograph of a stabilizer D obtained in Example 4.

The stabilizer of the present invention contains a bisphenol monoester represented by the following Formula (1).

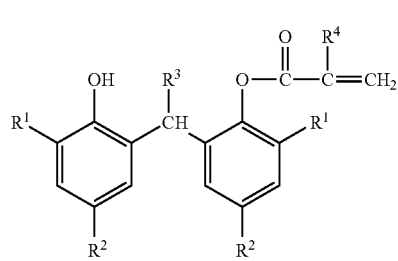

(1)

In the Formula (1) representing the bisphenol monoester used in the stabilizer of the present invention, $R^1$ and $R^2$ independently represents an alkyl group having 1 to 5 carbon atoms. Examples of the alkyl group include a methyl group, an ethyl group, an n-propyl group, an isopropyl group, an n-butyl group, an isobutyl group, a sec-butyl group, a tert-butyl group, an n-pentyl group, a tert-pentyl group and the like. In particular, $R^1$ is preferably an alkyl group having a tertiary carbon, that is, a tert-butyl group or a tert-pentyl group.

In the Formula (1) representing the bisphenol monoester used in the stabilizer of the present invention, $R^3$ represents a hydrogen atom or an alkyl group having 1 to 3 carbon atoms. Examples of the alkyl group include a methyl group, an ethyl group, an n-propyl group, and an isopropyl group, and among these, a methyl group is particularly preferable.

In the Formula (1) representing the bisphenol monoester used in the stabilizer of the present invention, $R^4$ represents a hydrogen atom or a methyl group.

Specific examples of the bisphenol monoester used in the stabilizer of the present invention include 2,4-di-tert-pentyl-6-[1-(3,5-di-tert-pentyl-2-hydroxyphenyl)ethyl]phenylacrylate, 2-tert-butyl-6-[1-(3-tert-butyl-2-hydroxy-5-methylphenyl)methyl]-4-methylphenylacrylate, 2-[1-(2-hydroxy-3,5-di-tert-pentylphenyl)ethyl]-4,6-di-tert-pentylphenylmethacrylate, 2,4-di-tert-butyl-6-[1-(3,5-di-tert-butyl-2-hydroxyphenyl)ethyl]phenylacrylate, 2,4-di-tert-butyl-6-[1-(3,5-di-tert-butyl-2-hydroxyphenyl)ethyl]phenylmethacrylate, 2-tert-butyl-6-[1-(3-tert-butyl-2-hydroxy-5-methylphenyl)ethyl]-4-methylphenylacrylate, 2-tert-butyl-6-[1-(3-tert-butyl-2-hydroxy-5-methylphenyl)propyl]-4-methylphenylacrylate, 2-tert-butyl-6-[1-(3-tert-butyl-2-hydroxy-5-propylphenyl)ethyl]-4-propylphenylacrylate, 2-tert-butyl-6-[1-(3-tert-butyl-2-hydroxy-5-isopropylphenyl)ethyl]-4-isopropylphenylacrylate and the like. Among these, because an excellent process stabilizing effect can be imparted to the thermoplastic polymer, 2,4-di-tert-pentyl-6-[1-(3,5-di-tert-pentyl-2-hydroxyphenyl)ethyl]phenylacrylate and 2-tert-butyl-6-[1-(3-tert-butyl-2-hydroxy-5-methylphenyl)methyl]-4-methylphenylacrylate are preferable.

The bisphenol monoester represented by Formula (1) can be manufactured by reaction of the bisphenol-based compound represented by the following Formula (2):

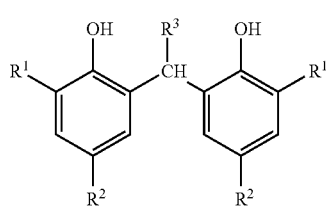

wherein $R^1$ to $R^3$ are the same as described above, with carboxylic acid or its derivatives. The bisphenol monoester is preferably purified, for example, through a purification method disclosed in Japanese Patent Laying-Open No. 04-327558 (Patent Document 3) (that is, crystallization in a mixed solvent of a first solvent selected from aromatic hydrocarbons having 6 to 12 carbon atoms and a second solvent selected from alcohols having 1 to 8 carbon atoms and aliphatic nitriles having 2 to 3 carbon atoms) after the above-described reaction.

Examples of the aromatic hydrocarbons having 6 to 12 carbon atoms, which are the first solvent used in the purification, include benzene, toluene, xylene, ethylbenzene, cumene, cymene, chlorobenzene and the like. Any of these aromatic hydrocarbons selected from the above-described aromatic hydrocarbons may be used alone, or two types or more thereof may be used in combination. Among these, toluene or xylene is preferably used, and xylene is particularly preferable.

Examples of the alcohols having 1 to 8 carbon atoms, which are the second solvent used in the purification, include methanol, ethanol, n-propanol, isopropanol, n-butanol, isobutanol, tert-butanol, n-pentanol, n-octanol, 2-ethylhexanol, cyclohexanol and the like. Further, examples of the aliphatic nitriles having 2 to 3 carbon atoms include acetonitrile and propionitrile. Any of these alcohols and aliphatic nitriles selected from the above-described alcohols and aliphatic nitriles may be used alone, or two types or more of them may be used in combination.

The bisphenol monoester available commercially may be, of course, used as the bisphenol monoester represented by the Formula (1) in the stabilizer of the present invention, and specifically, Sumilizer (trademark) GS (F) (manufactured by Sumitomo Chemical Co., Ltd.), Sumilizer (trademark) GS (manufactured by Sumitomo Chemical Co., Ltd.), Sumilizer (trademark) GM (manufactured by Sumitomo Chemical Co., Ltd.), and the like can be preferably used.

The stabilizer of the present invention contains the bisphenol-based compound represented by the following Formula (2) in addition to the above-described bisphenol monoester. This bisphenol-based compound is used also as a raw material when the bisphenol monoester represented by the Formula (1) described above is manufactured.

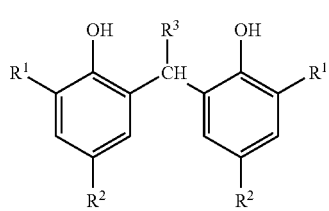

In the Formula (2) representing the bisphenol-based compound used in the stabilizer of the present invention, $R^1$ to $R^3$ are the same as $R^1$ to $R^3$ in the Formula (1), respectively.

Specific examples of the bisphenol-based compound used in the stabilizer of the present invention include 2,2'-ethylidenebis(4,6-di-tert-pentylphenol), 2,2'-methylenebis(6-tert-butyl-4-methylphenol), 2,2'-methylenebis(4,6-di-tert-butylphenol), 2,2'-methylenebis(4,6-di-tert-pentylphenol), 2,2'-ethylidenebis(4,6-di-tert-butylphenol), 2,2'-propylidenebis(6-tert-butyl-4-methylphenol), 2,2'-ethylidenebis(6-tert-butyl-4-methylphenol), 2,2'-ethylidenebis(6-tert-butyl-4-propylphenol, 2,2'-ethylidenebis(6-tert-butyl-4-isopropylphenol) and the like, and among these, because an excellent process stabilizing effect can be imparted to the thermoplastic polymer, 2,2'-ethylidenebis(4,6-di-tert-pentylphenol) and 2,2'-methylenebis(6-tert-butyl-4-methylphenol) are particularly preferable.

The bisphenol-based compound represented by the Formula (2) can be manufactured by condensing a corresponding 2,4-dialkylphenol with aldehydes for example. The above-described bisphenol-based compound is preferably purified, for example, through crystallization in a mixed solvent of a first solvent selected from aromatic hydrocarbons having 6 to 12 carbon atoms and a second solvent selected from alcohols having 1 to 8 carbon atoms and aliphatic nitriles having 2 to 3 carbon atoms after the above-described condensation reaction. Further, a bisphenol-based compound available commercially may be, of course, used as the bisphenol-based compound.

The stabilizer of the present invention contains the bisphenol monoester represented by the Formula (1) and the bisphenol-based compound represented by the Formula (2) so that the area of the bisphenol-based compound represented by the Formula (2) is 0.15 to 70 when the area of bisphenol monoester represented by the Formula (1) is set to be 100 in the chromatograph obtained by liquid chromatography analysis. Because the area of the above-described bisphenol-based compound is in the above-described range, the process stability of the thermoplastic polymer can be improved. Moreover, the content of the above-described bisphenol-based compound is preferably in a range of 0.15 to 50 with respect to 100 of the area of the above-described bisphenol monoester, and particularly preferably in a range of 0.18 to 40.

Conventionally known and appropriate additives may be, of course, added to the stabilizer of the present invention in a range of which the effect of the present invention is not hindered. Examples of such additives include an ultraviolet absorber, a light stabilizer, an antioxidant, a metal inactivator, a nucleating agent, a lubricant, an antistatic agent, a fire retardant, a filler, a pigment, a plasticizer, an anti-blocking agent, a surfactant, a processing aid, a foaming agent, an emulsifier, a brightener, a neutralizing agent such as calcium stearate and hydrotalcite, a binder and the like.

In the stabilizer of the present invention, the total amount of the bisphenol monoester represented by the Formula (1) and the bisphenol-based compound represented by the Formula (2) is preferably 90 parts by eight or more per 100 parts by weight of the stabilizer even if the additives as described above are added, and more preferably 95 parts by weight or more. In the case where the total amount of the above-described bisphenol monoester and the above-described bisphenol-based compound is less than 90 parts by weight, there is a fear that the process stabilizing effect becomes insufficient.

The form of the stabilizer of the present invention is not particularly limited. However, it is normally preferable that the form is a powder form, a granule form, a pellet form, a flake form and the like.

The method of manufacturing the stabilizer of the present invention is not particularly limited as long as the stabilizer is a mixture of the bisphenol monoester represented by the Formula (1) and the bisphenol-based compound represented by the Formula (2) (and the above-described appropriate additives, when needed). However, the stabilizer can be preferably manufactured through a method of obtaining a bisphenol monoester represented by the Formula (1) containing the bisphenol-based compound represented by the Formula (2), including the step of carrying out esterification reaction of a carboxylic acid-based compound represented by the following Formula (3):

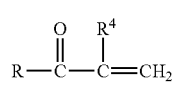

(3)

wherein $R^4$ is the same as described above, R represents a hydroxy group, a halogen atom, an alkoxy group having 1 to 4 carbon atoms, or a group represented by the following Formula (4):

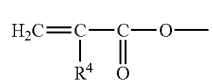

(4)

wherein $R^4$ is the same as described above, with the bisphenol-based compound represented by the Formula (2) in a method described in Japanese Patent Laying-Open No. 04-264051. The present invention also provides such a method of manufacturing the stabilizer of the present invention. In the method of manufacturing the stabilizer including the above-described esterification reaction step, the carboxylic compound represented by the Formula (3) is used in an amount of 0.3 to 0.6 mol, and preferably 0.4 to 0.6 mol, with respect to 1 mol of the bisphenol-based compound represented by the Formula (2).

Further, the present invention also provides a method of manufacturing a stabilizer, in which the bisphenol monoester represented by the Formula (1) and the bisphenol-based compound represented by the Formula (2) are mixed, and the amounts of the bisphenol monoester represented by the Formula (1) and the bisphenol-based compound represented by the Formula (2), to be mixed, are adjusted so that the area of the bisphenol-based compound represented by the Formula (2) is 0.15 to 70 when the area of bisphenol monoester represented by the Formula (1) is set to be 100 in the chromatograph obtained by liquid chromatography analysis of the obtained mixture. In this case, the stabilizer of the present invention is manufactured by mixing the bisphenol-based compound represented by the Formula (2) that has been isolated and purified, and the bisphenol monoester represented by the Formula (1) with a mixer such as a Henschel mixer, a super mixer, and a high-speed mixer. Moreover, the bisphenol-based compound represented by the Formula (2) is preferably mixed in an amount of 0.1 to 45 parts by weight, and more preferably 0.5 to 25 parts by weight, with respect to 100 parts by weight of the bisphenol monoester represented by the Formula (1).

Examples of the method of mixing the above-described appropriate additives into the stabilizer of the present invention include, for example, a method of mixing the bisphenol monoester represented by the Formula (1), the bisphenol-based compound represented by the Formula (2), and the additives with a mixer such as a container rotary mixer and a stirring type mixer, and a method of dissolving or dispersing the bisphenol monoester represented by the Formula (1), the bisphenol-based compound represented by the Formula (2), and the additives into one or more types of solvent selected from aromatic hydrocarbons having 6 to 12 carbon atoms, alcohols having 1 to 8 carbon atoms, and aliphatic nitriles having 2 to 3 carbon atoms, and then removing the solvent under reduced pressure.

The stabilizer of the present invention may be mixed as described above. However, the stabilizer is preferably molded into a granule form since it is difficult to generate dusts and the like. Specific examples include a method of obtaining a granule form stabilizer by mixing the bisphenol monoester represented by the Formula (1) and the bisphenol-based compound represented by the Formula (2) together with the above-described appropriate additives when needed (below, there is a case that this mixture is referred to as "the mixture") and granulating the mixture, a method of obtaining a flake form stabilizer by compressing and granulating the mixture with a compression granulator such as a roller compactor, a method of obtaining a pellet form stabilizer by melt-extruding the mixture with a single screw extruder or a multi-screw extruder or extruding the mixture with a semi-drying extruder such as a disk pelleter, and the like.

The present invention can provide a stabilizer that can improve the process stability of the thermoplastic polymer synergistically by compounding the stabilizer into the thermoplastic polymer compared with the case of using the bisphenol monoester represented by the Formula (1) and the bisphenol-based compound represented by the Formula (2) separately. Here, the improvement of the process stability can be evaluated by kneading and mixing the thermoplastic polymer composition compounded with the stabilizer of the present invention, molding the mixture into a pellet from, and then measuring the melt flow rate (MFR) value of the pellet using a melt indexer.

Here, the thermoplastic polymer, into which the stabilizer of the present invention is compounded, is not particularly limited, and examples thereof include a polypropylene-based resin such as a polypropylene homopolymer, a propylene-ethylene copolymer, and a propylene-ethylene-α olefin terpolymer; a polyethylene-based resin such as high-density polyethylene (HD-PE), low-density polyethylene (LD-PE), and linear low-density polyethylene (LLDPE), a ethylene-vinylacetate copolymer, and an ethylene-MMA copolymer; a methylpentene polymer; a polystyrene-based resin such as polystyrene, an acrylonitrile-styrene copolymer, a styrene-butadiene copolymer, a styrene-acrylonitrile-butadiene terpolymer, and a high-impact polystyrene; chlorinated polyethylene; polycholoropyrene; chlorinated rubber; polyvinyl chloride; polyvinylidene chloride; a methacrylic resin; an ethylene-vinyl alcohol copolymer; a fluorine resin; polyacetal; a grafted polyphenylene ether resin; a polyphenylene sulfide resin; polyurethane; polyamide; a polyester resin such as polyethylene terephthalate and polybutylene terephthalate; polycarbonate; polyacrylate; polysulfone; polyetheretherketone; polyethersulfone; an aromatic polyester resin; a diallylphthalate prepolymer; a silicone resin; 1,2-polybutadiene; polyisoprene; a butadiene-acrylonitrile copolymer; an ethylene-propylene copolymer; an ethylene-methylmethacrylate copolymer and the like. Among these, a polyethylene-based resin, a polypropylene-based resin, and a polystyrene-based resin are preferable due to good molding processiability, and a polypropylene-based resin and the polystyrene resin are particularly preferable.

Here, the polypropylene-based resin means polyolefin containing a structural unit originated from propylene, and specific examples include a crystalline propylene homopolymer, a propylene-ethylene random copolymer, a propylene-α-olefin random copolymer, a propylene-ethylene-α-olefin copolymer, a polypropylene-based block copolymer containing a polypropylene homopolymer component or a copolymer component mainly containing propylene, and a copolymer component of propylene and ethylene and/or α-olefin, and the like.

In the case of using a polypropylene-based resin as the thermoplastic polymer in the present invention, one type of the polypropylene-based resin may be used, or two or more types may be blended and used.

The α-olefin is normally α-olefin having 4 to 12 carbon atoms, and examples include 1-butene, 1-pentene, 1-hexene, 4-methyl-1-pentene, 1-octene, 1-decene and the like. The α-olefin is more preferably 1-butene, 1-hexene, and 1-octene.

Examples of the propylene-α-olefin random copolymer include a propylene-1-butene random copolymer, a propylene-1-hexene random copolymer, a propylene-1-octene random copolymer and the like.

Examples of the propylene-ethylene-α-olefin copolymer include a propylene-ethylene-1-butene copolymer, a propylene-ethylene-1-hexene copolymer, a propylene-ethylene-1-octene copolymer and the like.

Examples of a copolymer component mainly containing propylene in the polypropylene-based block copolymer containing a polypropylene homopolymer component or a copolymer component mainly containing propylene, and a copolymer component of propylene and ethylene and/or α-olefin include, for example, a propylene-ethylene copolymer component, a propylene-1-butene copolymer component, a propylene-1-hexene copolymer component and the like. Examples of the copolymer component of propylene and ethylene and/or α-olefin include, for example, a propylene-ethylene copolymer component, a propylene-ethylene-1-butene copolymer component, a propylene-ethylene-1-hexene copolymer component, a propylene-ethylene-1-octene copolymer component, a propylene-1-butene copolymer component, a propylene-1-hexene copolymer component, a propylene-1-octene copolymer component and the like. Moreover, the content of ethylene and/or α-olefin having 4 to 12 carbon atoms in the copolymer component of propylene and ethylene and/or α-olefin is normally 0.01 to 20% by weight.

Further, examples of the polypropylene-based block copolymer containing a polypropylene homopolymer component or a copolymer component mainly containing propylene, and a copolymer component of propylene and ethylene and/or α-olefin include, for example, a propylene-ethylene block copolymer, a (propylene)-(propylene-ethylene) block copolymer, a (propylene)-(propylene-ethylene-1-butene) block copolymer, a (propylene)-(propylene-ethylene-1-hexene) block copolymer, a (propylene)-(propylene-1-butene) block copolymer, a (propylene)-(propylene-1-hexene) block copolymer, a (propylene-ethylene)-(propylene-ethylene-1-butene) block copolymer, a (propylene-ethylene)-(propylene-ethylene-1-hexene) block copolymer, a (propylene-ethylene)-(propylene-1-butene) block copolymer, a (propylene-ethylene)-(propylene-1-hexene) block copolymer, a (propylene-1-butene)-(propylene-ethylene) block copolymer, a (propylene-1-butene)-(propylene-ethylene-1-butene) block copolymer, a (propylene-1-butene)-(propylene-ethylene-1-hexene) block copolymer, a (propylene-1-butene)-(propylene-1-butene) block copolymer, a (propylene-1-butene)-(propylene-1-hexene) block copolymer and the like.

In the case of using the polypropylene-based resin as the thermoplastic polymer in the present invention, it is preferable to use a crystalline propylene homopolymer and a polypropylene-based block copolymer containing a polypropylene homopolymer component or a copolymer component mainly containing propylene, and a copolymer component of propylene and ethylene and/or α-olefin having 4 to 12 carbon atoms. More preferably, a polypropylene-based block copolymer containing a polypropylene homopolymer component or a copolymer component mainly containing propylene, and a copolymer component of propylene and ethylene and/or α-olefin having 4 to 12 carbon atoms is used.

The stabilizer of the present invention is preferably compounded in an amount of 0.01 to 5 parts by weight, and more preferably 0.01 to 2 parts by weight, with respect to 100 parts by weight of the above-described thermoplastic polymer. In the case where the compounded amount of the stabilizer of the present invention is less than 0.01 parts by weight with respect to 100 parts by weight of the thermoplastic polymer, there is a fear that the process stabilizing effect becomes insufficient, and in the case where the compounded amount of the stabilizer of the present invention exceeds 5 parts by weight with respect to 100 parts by weight of the thermoplastic polymer, a bleeding phenomenon of which the stabilizer appears on the surface of polymer tends to easily occur.

The method of compounding the stabilizer of the present invention into a thermoplastic polymer is not particularly limited as long as it is a known method. However, examples include a method of dry blending a thermoplastic polymer and a stabilizer and then melt-extruding the mixture with an extruder, a method of obtaining a thermoplastic polymer in which a stabilizer is compounded by adding a solution, in which the stabilizer is dissolved into a solvent such as cyclohexane, to a polymer solution, in which a solution polymerization is completed, to remove the solvent, and the like.

The present invention also provides a thermoplastic polymer composition containing the thermoplastic polymer and 0.01 to 5 parts by weight of the above-described stabilizer of the present invention with respect to 100 parts by weight of the thermoplastic polymer. In such a thermoplastic polymer composition of the present invention, the process stability is improved compared with the conventional one as described above.

The present invention furthermore provides a method of stabilizing the thermoplastic polymer, in which the stabilizer of the present invention is compounded in an amount of 0.01 to 5 parts by weight with respect to 100 parts by weight of the thermoplastic polymer. According to such a method of stabilizing the thermoplastic polymer of the present invention, the process stability of the thermoplastic polymer can be improved compared with the above-described conventional one.

EXAMPLES

Referring to the Examples and Comparative Examples below, the present invention is described in more detail. However, the present invention is not limited to these Examples.

Example 1

A Stabilizer A of a powder form was prepared by mixing 99.92 g of 2,4-di-tert-pentyl-6-[1-(3,5-di-tert-pentyl-2-hydroxyphenyl)ethyl]phenylacrylate (Sumilizer GS(F) manufactured by Sumitomo Chemical Co., Ltd.) as a bisphenol monoester and 0.08 g of 2,2'-ethylidenebis(4,6-di-tert-pentylphenol) as a bisphenol-based compound with a mortar. When stabilizer A was subjected to liquid chromatography analysis, the area of the bisphenol-based compound with respect to 100 of the area of bisphenol monoester was 0.17.

Moreover, the liquid chromatography analysis was performed using Sumipax A-210EC (3 mm φ×15 cm, diameter of filler: 5 μm) as a column, and a mixed solution of water and acetonitrile as a mobile phase, through a method of measuring a retention time using an UV detector at 280 nm under a condition in which a state was held for 20 minutes after the ratio of acetonitrile in the mobile phase was increased by every 75 to 0.42%/minute and then the ratio became 100%.

Example 2

A Stabilizer B of a powder form was prepared in the same manner as in Example 1, except that 99.9 g of a bisphenol monoester and 0.1 g of a bisphenol-based compound were used. When stabilizer B was subjected to liquid chromatography analysis in the same manner as in Example 1, the area of the bisphenol with respect to 100 of the area of the bisphenol monoester was 0.19.

Example 3

A Stabilizer C of a powder form was prepared in the same manner as in Example 1, except that 99.5 g of a bisphenol monoester and 0.5 g of a bisphenol-based compound were used. When stabilizer C was subjected to liquid chromatography analysis in the same manner as in Example 1, the area of the bisphenol with respect to 100 of the area of bisphenol monoester was 0.77.

Example 4

A Stabilizer D of a powder form was prepared in the same manner as in Example 1, except that 98 g of a bisphenol monoester and 2 g of a bisphenol-based compound were used. When stabilizer D was subjected to liquid chromatography analysis in the same manner as in Example 1, the area of the bisphenol with respect to 100 of the area of bisphenol monoester was 3.68.

Here, FIG. 1 shows a liquid chromatograph of Stabilizer D obtained in Example 4. As shown in FIG. 1, two peaks (a peak 1 and a peak 2) can be observed at two points of a retention time of 48.642 minute and 58.325 minute in the liquid chromatograph of Stabilizer D. The area, height, and area % of these two peaks are shown in Table 1.

TABLE 1

| | RETENTION TIME | AREA | HEIGHT | AREA % |
|---|---|---|---|---|
| PEAK 1 | 48.642 | 178023 | 7240 | 3.553 |
| PEAK 2 | 58.325 | 4832900 | 180754 | 96.447 |
| TOTAL | | 5010922 | 187994 | 100.000 |

Example 5

A Stabilizer E of a powder form was prepared in the same manner as in Example 1, except that 80 g of a bisphenol monoester and 20 g of a bisphenol-based compound were used. When stabilizer E was subjected to liquid chromatography analysis in the same manner as in Example 1, the area of the bisphenol with respect to 100 of the area of the bisphenol monoester was 36.2.

Example 6

A Stabilizer F of a powder form was prepared in the same manner as in Example 1, except that 70 g of a bisphenol monoester and 30 g of a bisphenol-based compound were used. When stabilizer F was subjected to liquid chromatography analysis in the same manner as in Example 1, the area of the bisphenol with respect to 100 of the area of the bisphenol monoester was 60.6.

Comparative Example 1

A Stabilizer G of a powder form was prepared in the same manner as in Example 1, except that 99.95 g of a bisphenol monoester and 0.05 g of a bisphenol-based compound were used. When stabilizer G was subjected to liquid chromatography analysis in the same manner as in Example 1, the area of the bispheriol with respect to 100 of the area of the bisphenol monoester was 0.12.

Example 7

0.2 part by weight of Stabilizer A obtained in Example 1 and 0.05 part by weight of calcium stearate were dry-blended into 100 parts by weight of a propylene-ethylene block copolymer (MI: 9 to 10 g/10 minutes) (230° C., 2.16 kg) (manufactured by Sumitomo Chemical Co., Ltd.) as a thermoplastic polymer, kneaded and mixtured at 210° C. at a screw rotational frequency of 50 rpm using a single screw extruder having a diameter of 30 mm (VS30-28 type extruder manufactured by Tanabe Plastic Co., Ltd.), to obtain pellets made of a propylene composition.

5 g of the obtained pellet was retained for 15 minutes in a cylinder heated at 280° C. with a melt indexer (L217-E14011 manufactured by TechnolSeven Co., Ltd.), and then an MFR value was measured under a condition of 280° C. and 2.16 kg. The result is shown in Table 3.

Examples 8 to 12 and Comparative Example 2

The examples were performed in the same manner as in Example 7, except that Stabilizers B to G obtained in Examples 2 to 5 and Comparative Example 1 were used instead of Stabilizer A used in Example 7. The results of MFR measured are shown in Table 3.

Comparative Example 3

Figure 2:
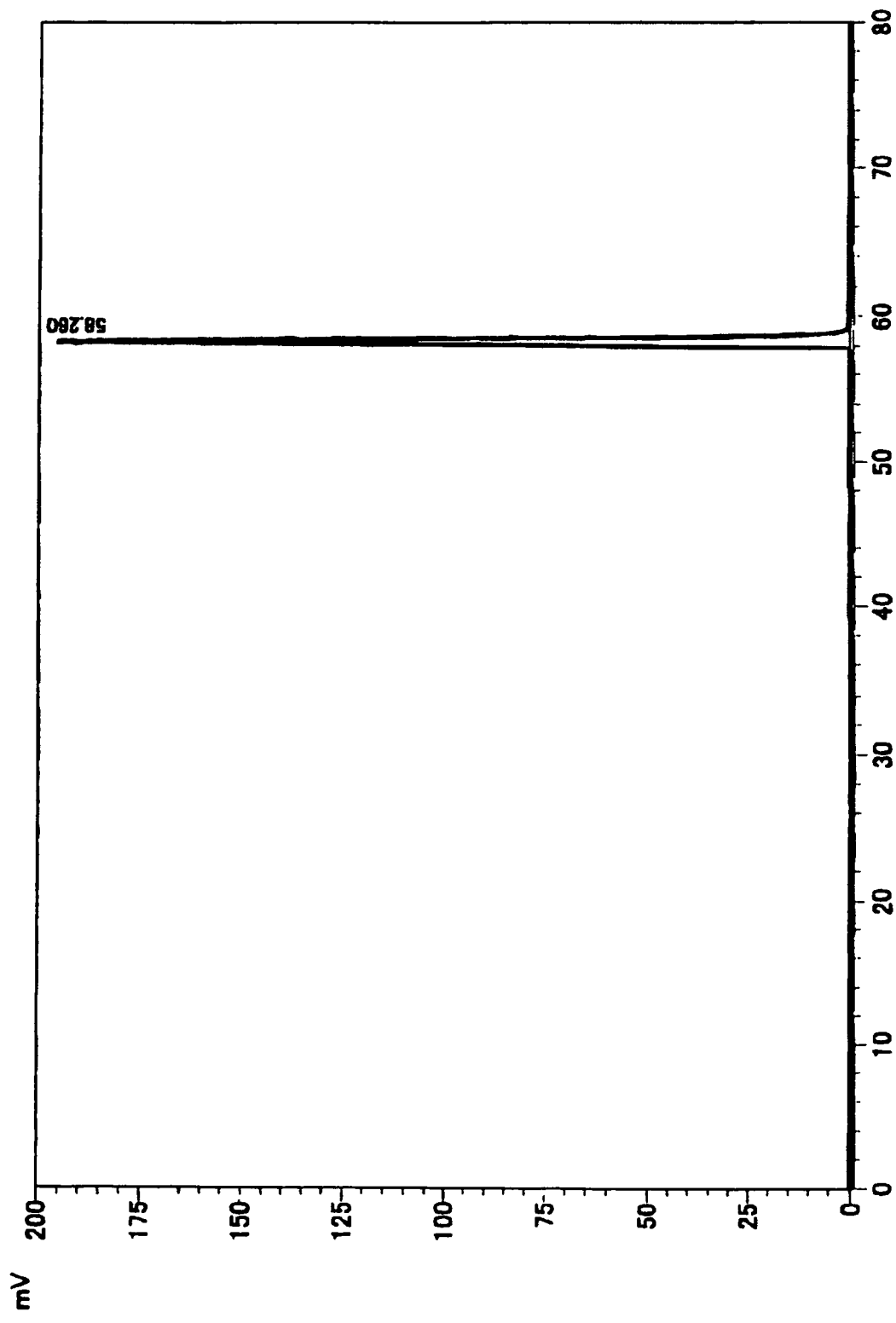
FIG. 2 is a liquid chromatograph of Sumilizer GS (F) (manufactured by Sumitomo Chemical Co., Ltd.) used in Comparative Example 3.

The example was performed in the same manner as in Example 7, except that Sumilizer GS (F) (manufactured by Sumitomo Chemical Co., Ltd.) was used instead of Stabilizer A used in Example 7. Moreover, FIG. 2 shows a liquid chromatograph of Sumilizer GS (F) used in Comparative Example 3. As shown in FIG. 2, only one peak (a peak 3) can be observed at a point of the retention time of 58.260 minute in the liquid chromatograph of Sumilizer GS (F). The area, height, and area % of this peak are shown in Table 2. Further, the result of a MFR measured is shown in Table 3 (in Table 3, the name of the stabilizer is described as "GS").

TABLE 2

| | RETENTION TIME | AREA | HEIGHT | AREA % |
|---|---|---|---|---|
| PEAK 3 | 58.260 | 5076943 | 195389 | 100.000 |
| TOTAL | | 5076943 | 195389 | 100.000 |

Comparative Example 4

The example was performed in the same manner as in Example 7, except that 2,2'-ethylidenebis(4,6-di-tert-pentylphenol) was used instead of Stabilizer A used in Example 7. The result of a MFR measured is shown in Table 3 (in Table 3, the name of the stabilizer is described as "EB").

Comparative Example 5

The example was performed in the same manner as in Example 7, except that a stabilizer was not compounded. The result of a MFR measured is shown in Table 3.

TABLE 3

| | STABILIZER | | PROCESS | |
|---|---|---|---|---|
| | | AREA OF | STABILITY | |
| | STABILIZER USED | BISPHENOL-BASED COMPOUND | MFR VALUE | RELATIVE VALUE |
| EXAMPLE 7 | STABILIZER A | 0.17 | 25.88 | 99.7 |
| EXAMPLE 8 | STABILIZER B | 0.19 | 25.64 | 98.8 |
| EXAMPLE 9 | STABILIZER C | 0.77 | 25.46 | 98.1 |
| EXAMPLE 10 | STABILIZER D | 3.68 | 25.39 | 97.8 |
| EXAMPLE 11 | STABILIZER E | 36.2 | 23.39 | 90.1 |
| EXAMPLE 12 | STABILIZER F | 60.6 | 24.69 | 95.1 |
| COMPARATIVE EXAMPLE 2 | STABILIZER G | 0.12 | 26.79 | 103.2 |
| COMPARATIVE EXAMPLE 3 | GS | <0.1 | 25.96 | 100.0 |
| COMPARATIVE EXAMPLE 4 | EB | — | 28.34 | 109.2 |
| COMPARATIVE EXAMPLE 5 | — | — | 52.80 | 203.4 |

In Table 3, "AREA OF BISPHENOL-BASED COMPOUND" means the area of the bisphenol-based compound when the area of the bisphenol monoester is set to be 100 in the liquid chromatography analysis. Moreover, in Comparative Example 4, "the area of the bisphenol-based compound" is not described because the bisphenol monoester is not contained in the stabilizer. Further, in Table 3, relative values are shown when the MFR value in Comparative Example 3 is set to be 100 as the process stability in addition to the MFR value. The smaller the MFR value is, the more excellent the process stability is meant to be.

Example 13

A Stabilizer H of a powder form was prepared in the same manner as in Example 1, except that 99.92 g of 2-tert-butyl-6-[1-(3-tert-butyl-2-hydroxy-5-methylphenyl)methyl]-4-methylphenylacrylate (Sumilizer GM manufactured by Sumitomo Chemical Co., Ltd.) as a bisphenol monoester and 0.08 g of 2,2'-methylenebis(6-tert-butyl-4-methylphenol) as the bisphenol compound were used. When stabilizer H was subjected to liquid chromatography analysis in the same manner as in Example 1, the area of the bisphenol with respect to 100 of the area of the bisphenol monoester was 0.21.

Example 14

A Stabilizer I of a powder form was prepared in the same manner as in Example 13, except that 98.0 g of a bisphenol monoester and 2.0 g of a bisphenol compound were used. When stabilizer I was subjected to liquid chromatography analysis in the same manner as in Example 1, the area of the bisphenol with respect to 100 of the area of the bisphenol monoester was 3.56.

Figure 3:
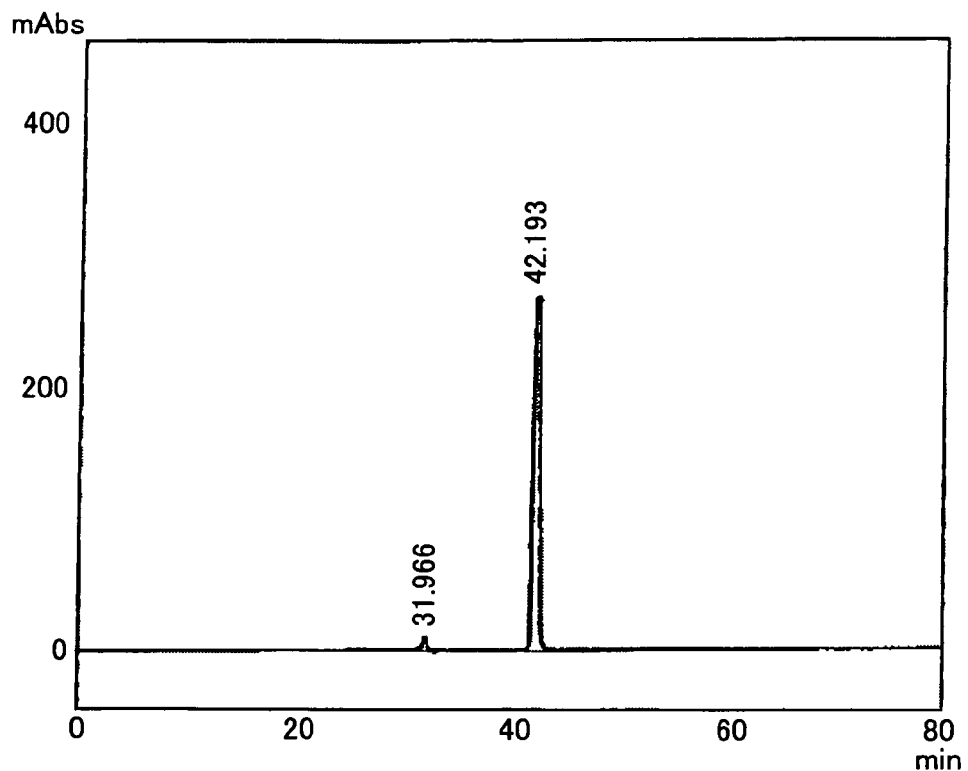
FIG. 3 is a liquid chromatograph of a stabilizer I obtained in Example 14.

Here, FIG. 3 shows a liquid chromatograph of Stabilizer I obtained in Example 14. As shown in FIG. 3, two peaks (a peak 1 and a peak 2) can be observed at two points of a retention time of 31.966 minute and 42.193 minute in the liquid chromatograph of Stabilizer I. The area, height, and area % of these two peaks are shown in Table 4.

TABLE 4

| | RETENTION TIME | AREA | HEIGHT | AREA % |
|---|---|---|---|---|
| PEAK 1 | 31.966 | 279139 | 10632 | 3.442 |
| PEAK 2 | 42.193 | 7831155 | 272346 | 96.558 |
| TOTAL | | 8110294 | 282978 | 100.000 |

Example 15

A Stabilizer J of a powder form was prepared in the same manner as in Example 13, except that 80.0 g of a bisphenol monoester and 20.0 g of a bisphenol compound were used. When stabilizer J was subjected to liquid chromatography analysis in the same manner as in Example 1, the area of the bisphenol with respect to 100 of the area of the bisphenol monoester was 42.7.

Comparative Example 6

A Stabilizer K of a powder form was prepared in the same manner as in Example 13, except that 99.95 g of a bisphenol monoester and 0.05 g of a bisphenol compound were used. When stabilizer K was subjected to liquid chromatography analysis in the same manner as in Example 1, the area of the bisphenol with respect to 100 of the area of the bisphenol monoester was 0.14.

Examples 16 to 18

The examples were performed in the same manner as in Example 7, except that Stabilizers H to K obtained in Examples 13 to 15 and Comparative Example 6 were used instead of Stabilizer A used in Example 7. The results of MFR measured are shown in Table 6.

Comparative Example 7

Figure 4:
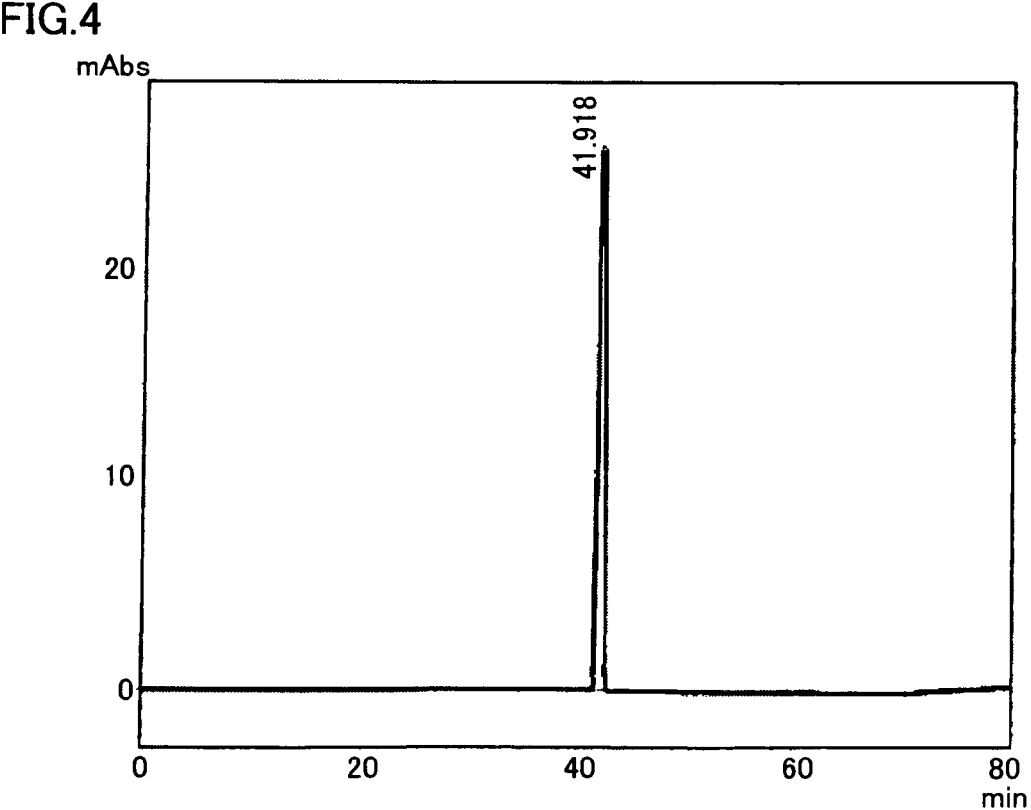
FIG. 4 is a liquid chromatograph of Sumilizer GM (manufactured by Sumitomo Chemical Co., Ltd.) used in Comparative Example 7.

The example was performed in the same manner as in Example 7, except that Sumilizer GM (manufactured by Sumitomo Chemical Co., Ltd.) was used instead of Stabilizer A used in Example 7. Moreover, FIG. 4 shows a liquid chromatograph of Sumilizer GM used in Comparative Example 7. As shown in FIG. 4, only one peak can be observed at a point of the retention time of 41.918 minute in the liquid chromatograph of Sumilizer GM. The area, height, and area % of this peak are shown in Table 5. Further, the result of a MFR measured is shown in Table 6 (in Table 6, the name of the stabilizer is described as "GM").

TABLE 5

|  | RETENTION TIME | AREA | HEIGHT | AREA % |
|---|---|---|---|---|
| PEAK | 41.918 | 824044 | 28838 | 100.000 |
| TOTAL |  | 824044 | 28838 | 100.000 |

Comparative Example 8

The example was performed in the same manner as in Example 7, except that 2,2'-methylenebis(6-tert-butyl-4-methylphenol) was used instead of Stabilizer A used in Example 7. The result of a MFR measured is shown in Table 6 (in Table 6, the name of the stabilizer is described as "MDP").

TABLE 6

|  | STABILIZER | | PROCESS STABILITY | |
|---|---|---|---|---|
|  | STABILIZER USED | AREA OF BISPHENOL-BASED COMPOUND | MFR VALUE | RELATIVE VALUE |
| EXAMPLE 16 | STABILIZER H | 0.21 | 24.64 | 99.3 |
| EXAMPLE 17 | STABILIZER I | 3.56 | 24.48 | 98.6 |
| EXAMPLE 18 | STABILIZER J | 42.7 | 24.19 | 97.4 |
| COMPARATIVE EXAMPLE 6 | STABILIZER K | 0.14 | 26.24 | 105.7 |
| COMPARATIVE EXAMPLE 7 | GM | <0.1 | 24.83 | 100.0 |
| COMPARATIVE EXAMPLE 8 | MDP | — | 26.63 | 107.3 |

Although the present invention has been described and illustrated in detail, it is clearly understood that the same is by way of illustration and example only and is not to be taken by way of limitation, the scope of the present invention being interpreted by the terms of the appended claims.

What is claimed is:

1. A stabilizer comprising, as a main component, a bisphenol monoester represented by the following Formula (1):

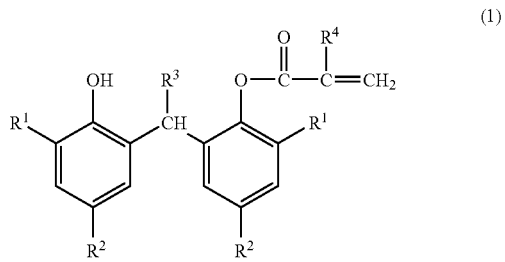

wherein $R^1$ is a tert-butyl group, $R^2$ is a methyl group, $R^3$ is a hydrogen atom and $R^4$ is a hydrogen atom, and a bisphenol-based compound represented by the following Formula (2):

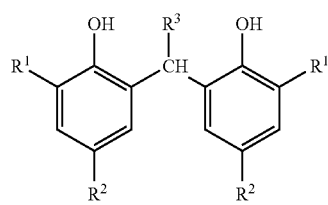

wherein $R^1$ to $R^3$ are the same as described above, wherein the area of the bisphenol-based compound represented by the Formula (2) is from 0.15 to 50 when the area of the bisphenol monoester represented by the Formula (1) is set to be 100 in a chromatograph obtained by liquid chromatography analysis of the stabilizer.

2. A method of manufacturing the stabilizer according to claim 1 comprising the steps of:

mixing the bisphenol monoester represented by the Formula (1) and the bisphenol-based compound represented by the Formula (2), and adjusting the amounts of the bisphenol monoester represented by the Formula (1) and the bisphenol-based compound represented by the Formula (2), to be mixed, so that the area of the bisphenol-based compound represented by the Formula (2) is from 0.15 to 50 when the area of the bisphenol monoester represented by the Formula (1) is set to be 100 in a chromatograph obtained by liquid chromatography analysis of the obtained mixture.

3. The method of manufacturing the stabilizer according to claim 2, wherein 0.1 to 45 parts by weight of the bisphenol-based compound represented by the Formula (2) is mixed into 100 parts by weight of the bisphenol monoester represented by the Formula (1).

4. A method of manufacturing the stabilizer according to claim 1 comprising the step of performing esterification reaction of a bisphenol-based compound represented by the following Formula (2):

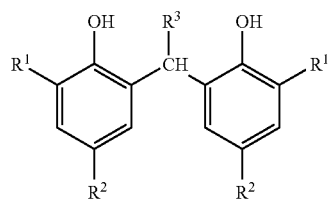

and a carboxylic acid-based compound represented by the following Formula (3):

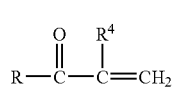

wherein $R^4$ is the same as described above, R represents a hydroxy group, a halogen atom, an alkoxy group having 1 to 4 carbon atoms, or a group represented by the following Formula (4):

(4)

wherein R⁴ is the same as described above, wherein 0.3 to 0.6 mol of the carboxylic acid-based compound represented by the Formula (3) is used with respect to 1 mol of the bisphenol-based compound represented by the Formula (2).

5. A thermoplastic polymer composition comprising 0.01 to 5 parts by weight of the stabilizer according to claim 1 with respect to 100 parts by weight of the thermoplastic polymer.

6. A method of stabilizing a thermoplastic polymer comprising adding 0.01 to 5 parts by weight of the stabilizer according to claim 1 to 100 parts by weight of the thermoplastic polymer.

* * * * *